United States Patent [19]
Bruso

[11] Patent Number: 4,597,493
[45] Date of Patent: * Jul. 1, 1986

[54] INSTRUMENT PROTECTOR

[75] Inventor: Loran H. Bruso, Ontario, Calif.

[73] Assignee: Warner-Lambert Company, Morris Plains, N.J.

[*] Notice: The portion of the term of this patent subsequent to Mar. 26, 2002 has been disclaimed.

[21] Appl. No.: 666,410

[22] Filed: Oct. 30, 1984

Related U.S. Application Data

[63] Continuation-in-part of Ser. No. 517,553, Jul. 27, 1983, Pat. No. 4,506,787.

[51] Int. Cl.⁴ ............................................. B65D 65/44
[52] U.S. Cl. .................................... 206/363; 206/478
[58] Field of Search ............... 206/363, 482, 439, 370, 206/371, 214, 478, 486; 229/68 R; 383/35; 493/86, 114, 473

[56] References Cited

U.S. PATENT DOCUMENTS

| | | | |
|---|---|---|---|
| 934,486 | 9/1909 | Walling | |
| 1,581,953 | 4/1926 | Jackson | 150/52 R |
| 2,472,028 | 5/1949 | Son | 21/105 |
| 3,013,656 | 12/1961 | Murphy, Jr. | 206/72 |
| 3,130,834 | 4/1964 | Korzaan | 206/80 |
| 3,278,020 | 10/1966 | Murphy | 206/80 |
| 3,487,922 | 1/1970 | Peck | 206/80 |
| 3,604,616 | 9/1971 | Greif | 229/55 |
| 3,640,450 | 2/1972 | Lieberman | 383/35 |
| 3,891,088 | 6/1975 | Huebner | 206/349 |
| 3,925,014 | 12/1975 | Langdon | 21/105 |
| 4,043,754 | 8/1977 | Sklar | 21/82 R |
| 4,135,868 | 1/1979 | Scheinholz | 422/310 |
| 4,142,632 | 3/1979 | Sandel | 206/363 |
| 4,229,420 | 10/1980 | Smith et al. | 422/310 |
| 4,385,692 | 5/1983 | Eldridge, Jr. | 206/363 |
| 4,506,787 | 3/1985 | Bruso | 206/363 |

Primary Examiner—William Price
Assistant Examiner—Jimmy G. Foster
Attorney, Agent, or Firm—Neil K. Nydegger

[57] ABSTRACT

A device for protecting medical instruments during sterilization and subsequent handling comprising a support member formed with a retaining loop for holding the instrument on the support member. A clear plastic sheet is joined at a portion of the margin of the support member to define a pocket into which the cutting edges of the medical instrument are placed for protection. A projection of the sheet which overhangs the open end of the pocket can be folded away from the support member to facilitate insertion of the instrument tips into the pocket. For jointed instruments, the support member may also have an attached flap which is folded to position between the open handles of the instrument and thereby separate the instrument's cutting edges during the sterilization process.

8 Claims, 8 Drawing Figures

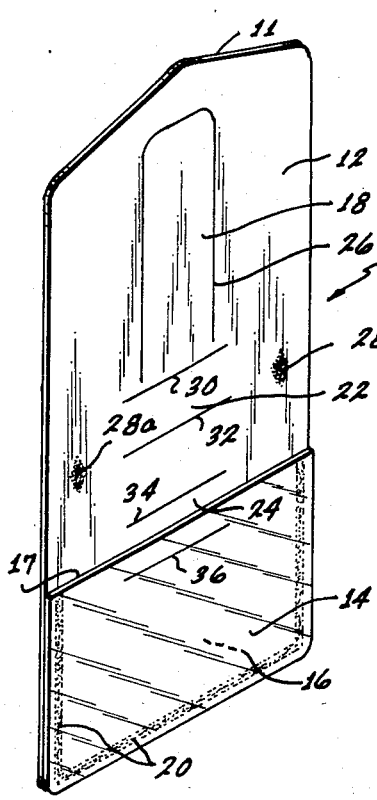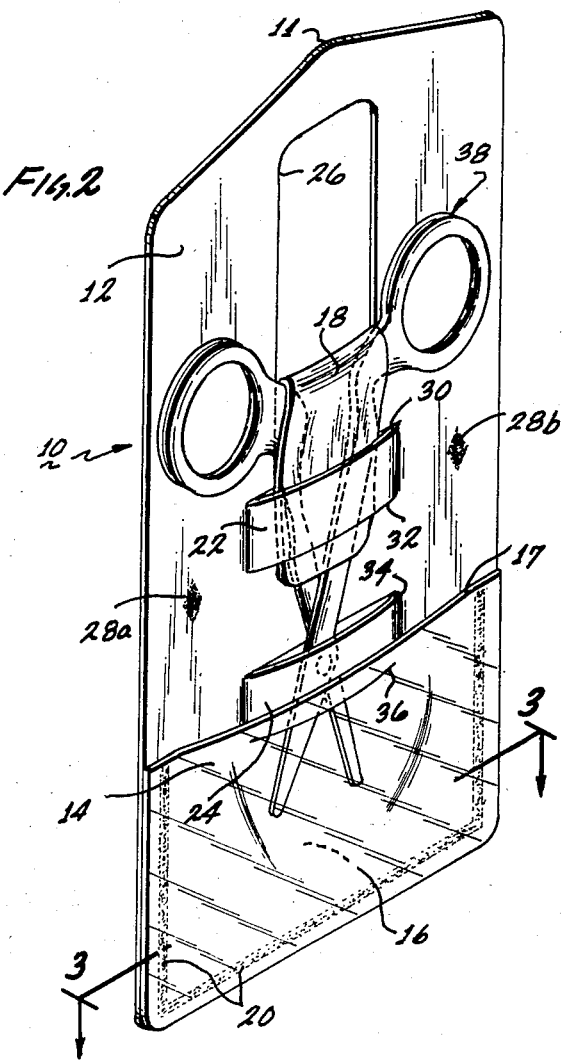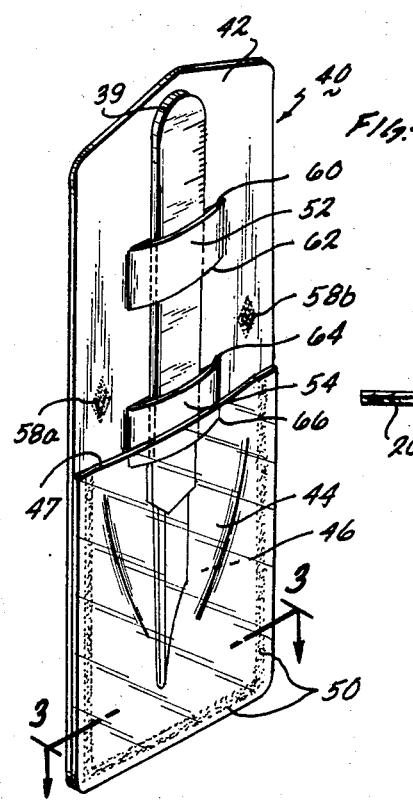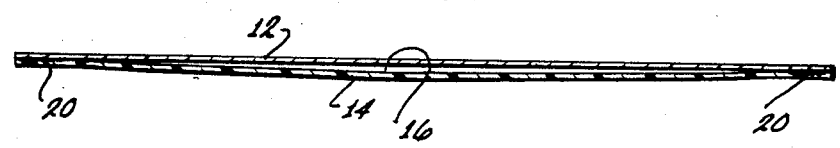

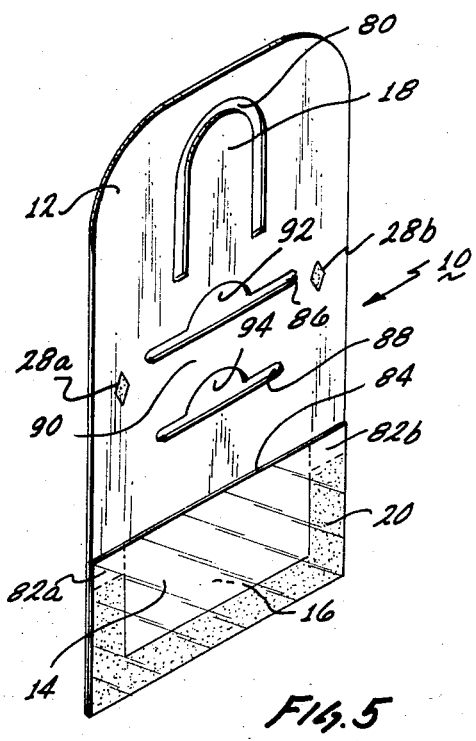
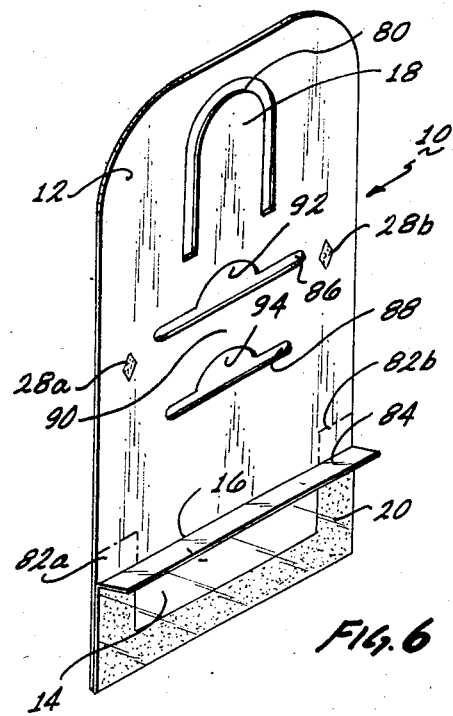
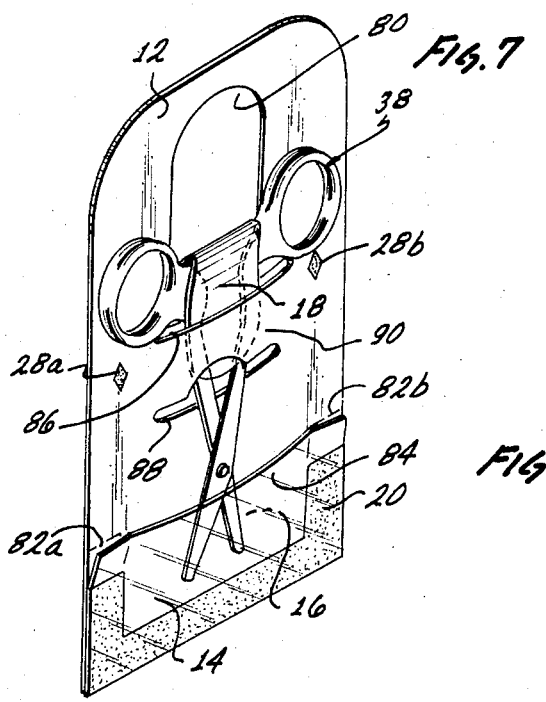
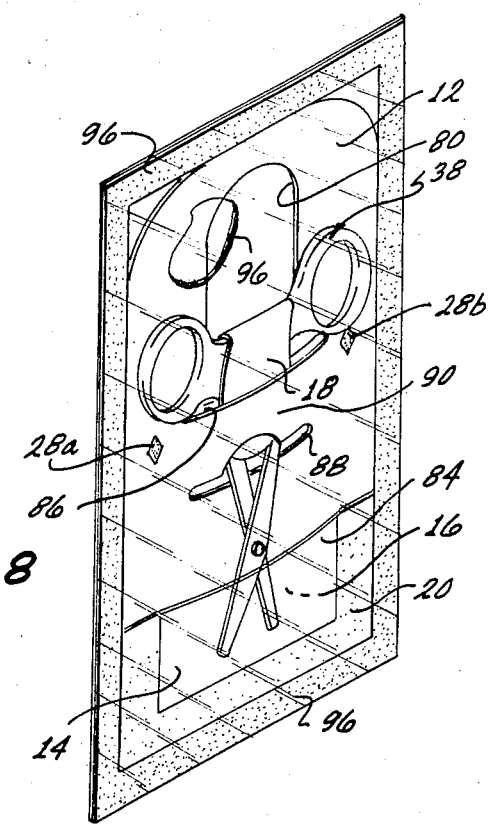

INSTRUMENT PROTECTOR

BACKGROUND OF THE INVENTION

This application is a continuation-in-part of my prior application entitled "Instrument Protector," Ser. No. 517,553, filed July 27, 1983 now U.S. Pat. No. 4,506,787. This invention relates generally to packaging techniques and retaining devices for medical instruments. More particularly, this invention relates to a retaining device usable for protecting medical instruments during and after sterilization while providing for visual identification of the instrument.

DESCRIPTION OF THE PRIOR ART

As is well known in the medical profession, the sterilization of precision medical instruments must be accomplished with certain purposes in mind. Basically, for both economic and efficiency reasons, such sterilization needs to be done in a manner which will ensure the most effective exposure of the instrument to the sterilizing medium while minimizing the possibility of contaminating the instrument prior to its use. Obviously, a major concern in this process is the actual handling of the instrument. In order to meet the need for effective handling of a medical instrument during sterilization, various packaging techniques have been proposed. The prior art devices, however, do not incorporate into one package all of the features which are deemed desirable for the most effective handling of a medical instrument between the time it is sterilized and its subsequent use.

One desirable feature of an instrument protector is that it immobilize the instrument. Such immobilization, particularly for medical instruments which are pointed or which have cutting edges, reduces the possibility of dulling or blunting their surfaces by contact with or rubbing against other surfaces. Another desirable feature is that the instrument protector present the instrument for sterilization in a configuration which will allow the greatest exposure of the instrument to the sterilizing medium. For jointed instruments this means supporting them with the blades or extension members in a separated condition. Additionally, it is desirable if some provision is made for easy identification of the instrument. Preferably, such identification can be done visually and thus obviate the use of external labels which may cause confusion if the protector is used with a different instrument. This last consideration is particularly important when it is envisioned that any particular embodiment of a sterilizable instrument protector, such as is disclosed by the present invention, can be used with a plurality of different instruments. Finally, use of the instrument protector must be effective regardless of the particular sterilization process utilized.

Several containers and devices for holding medical instruments during sterilization processes are well known in the art. For example, U.S. Pat. No. 4,229,420 issued to Smith et al., U.S. Pat. No. 4,043,754 issued to Sklar and U.S. Pat. No. 3,925,014 issued to Langdon are directed to surgical instrument racks for holding medical instruments during sterilization. These inventions are, however, designed for the collective sterilization of complete sets of instruments and do not provide the versatility and flexibiity achieved by sterilizing instruments in separate packages. Furthermore, when a plurality of instruments ae simultaneously sterilized on the racks of these inventions, the retrieval of one instrument requires the exposure and possible contamination of all the others.

U.S. Pat. No. 4,385,692 issued to Eldridge entitled "Surgical Instrument Tip Protector and Method of Manufacture" discloses a protector for individual surgical instruments made of a sterilizable fine pore foam having a transparent window portion to permit identification of the instrument. This patent does not, however, teach or suggest the provision of means for retaining jaw-type jointed instruments, such as a scissors, in a blade separated position during the sterilization process. Further, the protector disclosed in this patent is made of a fine pore foam which, if snagged by the instrument, could cause particulate contamination. Also, it does not provide for a protector having a rigid support that facilitates its insertion into and immobilization within a sterilizable envelope of the type disclosed in U.S. Pat. No. 3,604,616 issued to Greif. Additionally, the instrument protector disclosed in this patent does not provide a suitable substratum on which chemical indicator inks can be imprinted.

U.S. Pat. No. 4,142,632 to Sandel entitled "Surgical Instrument Holder and Instrument Tip Protector Device" discloses a device made of a reticulated material which employs straps to hold an instrument thereon. Further, this patent suggests doubling back part of its base member and pushing it between the open handles of a surgical scissors to maintain the scissors tip portions in an open position. However, unlike the present invention, this patent does not employ a flap, integral with the base of the device, which can be folded and wedged between the open handles of the instrument and then inserted under the strap to secure the jointed instrument to the base of the device.

For non-jointed instruments, such as scalpels and probes, the concerns are essentially the same as those discussed previously. With these instruments, however, the primary concern is to provide a stable support for the instrument which immobilizes the instrument on the support while permitting visual identification of the instrument. Whereas, U.S. Pat. No. 3,487,922 issued to Peck is directed to a cutlery display package having a transparent sheath, this patent does not suggest that its invention be used for sterilization of medical instruments. Moreover, it has certain distinguishable structural differences from the present invention. Specifically, the patent to Peck does not teach or suggest the use of die cut slits in the support to form a retaining strap for the instrument being protected.

Insofar as containers are concerned, U.S. Pat. No. 3,604,616 issued to Greif discloses a peel-open sterilizable envelope for retaining articles before, during and after sterilization. The patent also provides for an envelope which maintains sterility of the envelope's contents for extended periods of time. Although the invention of U.S. Pat. No. 3,604,616 allows for individual treatment of medical instruments, it is not teach or suggest means which would ease insertion of the instrument into the sterilizable envelope. Also, the patent does not teach a rigid support for immobilizing the medical instrument during the sterilization process.

Another desirable feature for an instrument protector is the ability to incorporate into the invention the use of chemical indicators that signify when the sterilization process has been completed. Typically, such indicators are specially formulated gas sensitive or steam sensitive inks of a type respectively disclosed in U.S. Pat. No. 3,098,751 issued to Huych et al. and U.S. Pat. No.

2,118,144 issued to Berman et al. Such inks are particularly useful with the instrument protector of the present invention insofar as they signify when the instrument has been exposed to a particular sterilizing condition. Whereas the present invention easily incorporates these inks, an instrument protector which is made with a foam, such as the device disclosed in U.S. Pat. No. 4,385,692 issued to Eldridge, would not provide the proper substratum for a chemical indicator ink.

Yet another desirable feature for an instrument protector is the added protection it can give against an inadvertent puncturing of the outer sterilizable envelope by the instrument's sharp or pointed surfaces. In the present invention, it is contemplated that the instrument's sharp and pointed surfaces will be sufficiently enclosed by appropriate materials to help guard against such an inadvertent puncturing.

In light of the above, it is an object of the present invention to provide an instrument protector having a rigid back for easy insertion into a peel pouch type sterilizable envelope. Additionally, the rigid back provides an appropriate substratum for chemical indicator inks. It is another object of the present invention to provide a means for holding jaw-type or jointed instruments in the blade separated position. Still another object of the present invention is to immobilize instruments within the sterilizable envelope during the sterilization process. A further object of the invention is to provide an inexpensive, easily manufactured instrument protector made of materials which have low particulate levels and which provide extra protection against a puncturing of the outer sterilizable envelope by the sharp or pointed surfaces of the instrument. Another object of the present invention is to provide an instrument protector with means that facilitate the insertion and placement of an instrument into the protector. Additionally, it is an object of the present invention to provide for a transparent pocket that allows easy identification of the medical instrument while it is held within the instrument protector.

SUMMARY OF THE INVENTION

A preferred embodiment of the novel instrument protector includes a support member having a retaining strap formed thereon for holding the instrument on the support member. A transparent film overlies a portion of the support member and is joined thereto at the margin of the support member to form a pocket into which the tip of the medical instrument is placed for protection. A portion of the transparent film is left unattached at the open end of the pocket to form a projection which can be peeled, lifted, rolled or folded back from the support member to ease and facilitate the insertion of an instrument's tips into the pocket. The support member may also be formed with a flap. For jointed medical instruments, such as a scissors, the flap can be folded and retained in position between the handles of the instrument to thereby positively keep and immoblilize the blades in a separated condition during sterilization.

An alternate embodiment of the novel instrument protector is contemplated for use with a monadic instrument. In the alternate embodiment, the flap need not be used or it can be eliminated.

The novel features of this invention, as well as the invention itself, both as to its organization and operation will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of an embodiment of the instrument protector;

FIG. 2 is a perspective view of the embodiment of FIG. 1 shown supporting a jointed medical instrument;

FIG. 3 is a cross-sectional view of the instrument protector on the line 3—3 of FIG. 2 and FIG. 4;

FIG. 4 is a perspective view of an alternate embodiment of the instrument protector shown supporting a monadic instrument;

FIG. 5 is a perspective view of another embodiment of the instrument protector;

FIG. 6 is a perspective view of the embodiment of the instrument protector of FIG. 5 configured for placement of an instrument on the protector;

FIG. 7 is a perspective view of the alternate embodiment of the instrument protector of FIG. 5 shown supporting a jointed medical instrument; and FIG. 8 is a perspective view of the instrument protector shown supporting a jointed medical instrument and inserted into a sterilizable envelope.

DESCRIPTION OF THE PREFERRED EMBODIMENT

Referring to FIG. 1, there is shown, generally at 10, the instrument protector of the present invention. In the preferred embodiment of the instrument protector 10, the support member 12 is made from a semi-rigid material such as paper, cardboard, plastic or any other sheet stock which can withstand sterilization conditions. The support member 12 is generally rectangular in shape, but it may be formed with a taper 11 at one end of the support member 12 to facilitate insertion of the instrument protector into a sterilization envelope such as of the type disclosed in U.S. Pat. No. 3,604,616.

As can be seen in both FIG. 1 and FIG. 2, the support member 12 is constructed with die cut slits 30, 32, 34 and 36. Slits 30 and 32 are cut in order to form an upper retaining strap 22. Likewise, slits 34 and 36 are cut to form a lower retaining strap 24. In another embodiment of the instrument protector as shown in FIG. 5 and FIG. 6, the lower retaining strap 24 can be eliminated. Also, in place of the slits 30 and 32, the support member 12 can be die cut with generally parallel slots 86 and 88 to form a retaining strap 90. As seen in FIG. 5 or FIG. 6, slots 86 and 88 can be formed with respective areas of increased width 92 and 94 to further facilitate placement of a medical instrument under retaining strap 90 on the support member 12.

The flap 18, shown in both FIG. 1 and FIG. 2, is formed by a die cut along the line 26. As seen in another embodiment of the present invention in FIGS. 5 and 6, flap 18 can also be formed by a U-shaped die cut slot 80. Regardless whether flap 18 is formed as shown in FIGS. 1 and 2 or as shown in FIGS. 5 and 6, its function is to immobilize a jointed instrument in a blades spread configuration for a purpose to be subsequently discussed in greater detail.

As best seen in FIGS. 1 and 2, support member 12 serves as a substratum for the chemical indicators 28a and 28b which can be applied to the support member 12 by any means well known in the art. For the preferred embodiments, indicator 28a is a gas sensitive ink of the type disclosed in U.S. Pat. No. 3,098,751 and chemical indicator 28b is a steam sensitive ink of the type disclosed in U.S. Pat. No. 2,118,144.

A sheet 14 made of a transparent material, such as clear plastic, is attached at the margin of support member 12 along a line 20 by any means well known in the art, such as by heat sealing. This combination of the sheet 14 on support member 12 is for the purpose of forming a pocket 16. As can be best seen in FIG. 3, the pocket 16 is formed by the support member 12 and the sheet 14. In the preferred embodiments of the present invention, the lip 17 of the pocket 16 is not joined with the support member 12. As seen in FIGS. 1, 2 or 3 lip 17 is positioned on the support member 12 over the lower retaining strap 24 to lie intermediate die cut slit 34 and die cut slit 36. This structure is provided to facilitate insertion of the blade portion of a medical instrument such as the scissors 38 into the pocket 16. In another embodiment of the instrument protector 10, shown in FIGS. 5, 6 and 7, sheet 14 is not attached to support member 12 in regions 82a and 82b. This unattached portion of sheet 14 thereby forms a projection 84. As best seen in FIG. 6, projection 84 can be lifted or folded away from support member 12 at the open end of pocket 16 to form a wider opening for the pocket 16 that facilitates insertion of the tips of a medical instrument, such as scissors 38, into the pocket 16.

In its operation the instrument protector 10 is intended to rigidly retain a jointed medical instrument such as the scissors 38 shown in FIG. 2. In preparing the scissors 38 for sterilization with use of the instrument protector 10, the scissors 38 would be sequentially woven through slit 30, slit 32, slit 34 and slit 36 to be in position as shown in FIG. 2. As can be best seen in FIG. 2 after the medical instrument 38 has been woven through the slits 30, 32, 34 and 36 as described above, the tip end of the instrument lies within the pocket 16 defined by sheet 14 and support member 12. For jointed medical instruments, such as scissors 38, the handles thereof can be spread to consequently spread the blades of the instrument. To retain the medical instrument in the blade separated condition, the flap 18 is folded between the handles of scissors 38 as shown in FIG. 2. Flap 18 is then sequentially inserted through the slit 30 and the slit 32 of the upper retaining strap 22. Therefore, as shown clearly in FIGS. 2, 7 and 8, the flap 18 is held under the respective strap 22 or strap 90 and wedged against the parted handles of scissors 38 to secure same. In this configuration, the instrument protector 10 rigidly holds a jointed medical instrument, such as the scissors 38, and is ready for insertion into a sterilizable bag such as of the type disclosed in U.S. Pat. No. 3,604,616. Further, in the configuration where flap 18 is folded to retain scissors 38 on instrument protector 10, the protector 10 presents a relatively flat profile which avoids bulges that could inhibit its insertion and positioning into a sterilizable bag.

In using the instrument protector 10, as shown in FIG. 5, for the sterilization of a medical instrument such as scissors 38, scissors 38 would be sequentially woven through slots 86 and 88. As can be best seen in FIG. 7 after scissors 38 has been woven through slots 86 and 88, the tips of scissors 38 need to be positioned into the pocket 16. This can be facilitated by folding or lifting projection 84 away from the support member 12 into a configuration as shown in FIG. 6. With projection 84 folded away from the support member 12, the opening to pocket 16 is widened and the tips of scissors 38 can be more easily inserted into the pocket 16. For jointed medical instruments, such as scissors 38, the handles thereof can then be spread to consequentlially spread the blades of the instrument. As with the embodiment of the present invention previously discussed, to retain the scissors in the blades separated condition, the flap 18 can be folded between the handles of scissors 38. As shown in FIG. 7 flap 18 is then sequentially inserted through slot 84 and slot 86 to be held under the strap 90 and wedged between the parted handles of scissors 38 to secure same. In this configuration the instrument protector 10 rigidly holds a medical instrument and is ready for insertion into a sterilizable bag 96.

For purposes of illustration, FIG. 8 shows a jointed instrument mounted on an instrument protector 10 which has been inserted into a sterilization bag 96. Dimensioning of the support member 12 to conform with the inner dimensions of the sterilizable bag 96, as shown in FIG. 8, will contribute to the stability of the scissors 38 during the sterilization process by preventing movement of the instrument protector within the bag during the sterilization process.

After sterilization, when the medical instrument is to be used, the instrument protector 10, with the medical instrument retained thereon, is removed from the envelope. Release of the tab 18 from the upper retaining strap 22 frees the medical instrument so it can be removed from the instrument protector 10 and used for its intended purpose.

In an alternate embodiment of the instrument protector shown in FIG. 4 and generally identified by the referenced character 40, it can be appreciated that there is no need for the flap 18 shown in FIGS. 1, 2 5 or 6. In all other respects the instrument protector 10 and the instrument protector 40 are substantially similar. The alternate embodiment is, however, better suited when the medical instrument is not jointed and is, instead, a monadic instrument of the scalpel or probe type. More specifically, the alternate embodiment of an instrument protector 40 comprises a support member 42 which is of a semi-rigid material similar to the material described for instrument protector 10. In the instrument protector 40, the support member 42 is formed with the die cut slits 60, 62, 64 and 66. Respectively, slits 60 and 62 form an upper retaining strap 52 and the slits 64 and 66 form a lower retaining strap 54. Also, support member 42 has provision for incorporating chemical indicators 58a and 58b. The indicators 58a and 58b are substantially similar to the indicators 28a and 28b previously discussed and are preferably made from the same indicator inks.

Like instrument protector 10, the instrument protector 40 includes a clear plastic sheet 44 which is heat sealed to the support member 42 along the line 50. This joining of the sheet 44 to instrument protector 40 forms the pocket 46. A medical instrument, such as the scalpel 39 shown in FIG. 4, when prepared for sterilization, is sequentially woven through slits 60, 62, 64 and 66. Thus, positioned as shown in FIG. 4, the blade end of scalpel 39 is located within the pocket 46. As can be best appreciated by reference to FIG. 4, insertion of the medical instrument into pocket 46 is facilitated if the lip 47 of pocket 46 lies intermediate the slit 64 and 66 of the lower retaining strap 54.

It should be recognized by the person of ordinary skill that the alternate embodiment of the present invention for monadic instruments, generally indicated 40 in FIG. 4, can have its retaining straps 52 and 54 formed by widened slots such as the slots 86 and 88 previously described and shown in FIGS. 5, 6 and 7. Also, transparent sheet 44 may be left unattached to support member 42 in appropriate regions at the margin of support member 42 to form a projection similar to the projection 84 previously discussed and for the purposes as previously described.

A medical instrument, such as scalpel 39 in the configuration shown in FIG. 4, is prepared for sterilization and can be inserted into a sterilizable envelope such as of the type described in U.S. Pat. No. 3,604,616. When needed the sterilized instrument, together with the instrument protector 40, can be removed from the sterilizable envelope and used for its intended purpose.

While the particular instrument protector as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. A device insertable into an envelope for immobilizing and protecting a jointed medical instrument of operatively associated parts within the envelope with parts thereof apart during a sterilization process which comprises:
   a support member having a pair of generally parallel transverse slots forming an integral strap for holding the removable instrument against said support member; and
   a transparent sheet overlying a portion of said support member and joined thereto along a sufficient portion of the margin of said support member to form an open-ended pocket thereover and having a projection of said sheet overhanging the open end of said pocket which can be folded away from said support member to facilitate insertion of the instrument tips into said pocket.

2. A device as recited in claim 1 further comprising an integral flap formed by partial severance of said support member and positioned for folding between the parted handles of said jointed instrument and inserted under said integral strap to be sandwiched between said strap and the parted handles of the jointed instrument to keep the handles and their associated tips respectively spaced apart in a separated condition.

3. A device as recited in claim 1 wherein at least one of said generally parallel transverse slots has a region of increased size for easing insertion of the instrument through said slot.

4. A device as recited in claim 2 wherein at least one of said generally parallel transverse slots has a region of increased size for easing insertion of the instrument through said slot.

5. A device as recited in claim 3 wherein said support member is a semi-rigid non-porous material.

6. A device as recited in claim 4 wherein said support member is a semi-rigid non-porous material.

7. A device insertable into an envelope for immobilizing and protecting a jointed medical instrument of operatively associated parts within the envelope with parts thereof apart during a sterilization process which comprises:
   a semi-rigid non-porous support member having a pair of generally parallel transverse slots forming an integral strap for holding the removable instrument against said suport member, at least one of said generally parallel transverse slots having a region of increased size for easing insertion of the instrument through said slot;
   an integral flap formed by partial severance of said support member and being positioned for folding between the parted handles of said jointed instrument and inserted under said integral strap to be sandwiched between said strap and the parted handles of the jointed instrument to keep the handles and their associated tips respectively spaced apart in a separated condition;
   a transparent sheet overlying a portion of said support member and joined thereto along a sufficient portion of the margin of said support member to form an open-ended pocket thereover and having a projection of said sheet overhanging the open end of said pocket which can be folded away from said support member to facilitate insertion of the instrument tips into said pocket; and
   a chemical indicator ink imprinted on said support member for indicating exposure of the medical instrument to a sterilization process.

8. A method for manufacturing a device insertable into an envelope for immobilizing and protecting a jointed medical instrument of operatively associated parts within the envelope with parts thereof apart during a sterilization process comprising the steps of:
   a. providing a support member of semi-rigid non-porous material;
   b. die cutting a pair of generally parallel transverse slots to form an integral strap for holding the removable instrument against said support member, at least one of said generally parallel transverse slots having a region of increased size for easing insertion of the instrument through said slot;
   c. partially severing said support member to form an integral flap positioned for folding between the parted handles of said jointed instrument and insertion under said integral strap to sandwich said flap between said strap and the parted handles of the jointed instrument to keep the handles and their associated tips respectively spaced apart in a separated condition;
   d. bonding a transparent sheet over a portion of said support member along a sufficient portion of the margin of said support member to form an open-ended pocket thereover and having a projection of said sheet overhanging the open end of said pocket which can be folded away from said support member to facilitate insertion of the instrument tips into said pocket; and
   e. imprinting a chemical ink on said support member for indicating exposure of the medical instrument to a sterilization process.

* * * * *